United States Patent [19]
Onofusa et al.

[11] Patent Number: 5,186,895
[45] Date of Patent: Feb. 16, 1993

[54] METHOD AND APPARATUS FOR AUTOMATIC ANALYSIS OF FLUID COMPOSITION INVOLVING A TIME-DEPENDENT VARIATION THEREOF

[75] Inventors: Mitsuo Onofusa, Kanagawa; Nobuyoshi Hashimoto, Yokohama; Kimiteru Tagawa, Tokyo; Michiro Hagiwara, Hiratsuka, all of Japan

[73] Assignee: Mitsui Toatsu Chemicals, Incorporated, Tokyo, Japan

[21] Appl. No.: 656,006

[22] Filed: Feb. 15, 1991

[30] Foreign Application Priority Data

Jun. 16, 1989 [JP] Japan .................................. 1-152430

[51] Int. Cl.⁵ .................... G01N 31/16; G01N 27/02; G01N 33/20
[52] U.S. Cl. ........................................ 422/67; 422/62; 422/68.1; 422/75; 422/76; 422/82.01; 422/82.05; 436/51; 436/55; 436/84; 436/163; 436/807; 204/153.23; 204/405
[58] Field of Search .................... 422/62, 63, 67, 68.1, 422/75, 76, 82.01, 82.05; 436/51, 55, 84, 163, 177, 179, 807; 204/153.23, 405

[56] References Cited

U.S. PATENT DOCUMENTS

| | | | |
|---|---|---|---|
| 2,953,440 | 9/1960 | Claudy | 422/62 |
| 3,447,906 | 6/1969 | Zimmerli | 422/75 |
| 3,649,205 | 3/1972 | Shirakawa et al. | 422/62 |
| 3,668,934 | 6/1972 | Hulley | 73/421 |
| 3,723,062 | 3/1973 | Dahms | 422/75 X |
| 3,878,059 | 4/1975 | Wechter et al. | 422/75 X |
| 4,289,745 | 9/1981 | Patil | 106/459 X |
| 4,292,294 | 9/1981 | Patil et al. | 106/459 X |
| 4,726,931 | 2/1988 | Benet et al. | 422/62 X |
| 4,749,552 | 6/1988 | Sakisako et al. | 422/62 X |
| 4,835,707 | 5/1989 | Amano et al. | 422/62 X |
| 4,894,345 | 1/1990 | Metzger et al. | 436/179 X |
| 4,950,610 | 8/1990 | Tittle | 436/163 |

FOREIGN PATENT DOCUMENTS

0259257 of 1988 European Pat. Off. .

OTHER PUBLICATIONS

Patent Abstracts of Japan, vol. 5, No. 156 (C-074), Oct. 6, 1981.
Abstract of Japanese Patent Application 53-87792.
57-99157 Patent Abstracts of Japan, C126, vol. 6, No. 186.
58-162852 Patent Abstracts of Japan, P245, vol. 7, No. 290.
56-129837 Patent Abstracts of Japan, P096, vol. 6, No. 2.
58-85164 Patent Abstracts of Japan, P216, vol. 7, No. 184.
56-81443 Patent Abstracts of Japan, P081, vol. 5, No. 150.
Abstract of Japanese Patent 47-31223.

Primary Examiner—James C. Housel
Assistant Examiner—Arlen Soderquist
Attorney, Agent, or Firm—Fisher, Christen & Sabol

[57] ABSTRACT

An automatic analytical apparatus in which a series of operations ranging from the sampling into a treating receptacle, pretreatment, analysis and discharge of a fluid sample to the preparation for the next analysis are repeated automatically in order, wherein the time-dependent variation of the composition is traced successively. This permits the presence of the composition variation or the course of the composition variation to be confirmed or the composition variation to be controlled, automatically.

9 Claims, 6 Drawing Sheets

METHOD AND APPARATUS FOR AUTOMATIC ANALYSIS OF FLUID COMPOSITION INVOLVING A TIME-DEPENDENT VARIATION THEREOF

This is a continuation-in-part application of International PCT Application No. JP90/00790, filed on Jun. 16, 1990.

BACKGROUND OF THE INVENTION

1. Field of the Invention

This invention relates to a method and apparatus for confirming or controlling the presence of composition variation or the variation course by analyzing automatically and frequently the time-dependent variation of the composition of a fluid, which involves a time-dependent variation of composition, in various reactors and stills.

2. Background Art

Continuous detection or analysis of the composition of liquid components, for example, in a reactor for conducting a variety of chemical reactions or in a distillation column, has been practiced to data in a few cases under specific conditions. In one of the cases, for instance, there exists a sensor capable of direct detection of the characters specific to the properties of an intended component, while in another, a specific means of instrumental analysis is available which can analyze reaction liquids successively in a short period of time without any prior treatment, like gas chromatography and liquid chromatography.

However, these available detection procedures are actually limited to only a few choices among a number of analytical techniques. One of the reasons is that the sensor as described above has not been developed yet, or that the troublesome pre- and post-treatments of samples required for the adequate operation of a sensor make it difficult to automate these treatments and hence always need manual help, thus failing in frequent and continuous detection. The second reason is that the analytical method itself is complicated, though established as a procedure for analysts, so that the analytical instrument for effecting the method has not been developed.

In various reactions, particularly in batch reactions, on the other hand, it is desired to detect frequently the time-dependent variation of the reaction rate and thereby to confirm the progress of the reaction. Further, it has become necessary to improve the quality and function of the product by allowing the reaction to follow its predetermined or intended desirable reaction course, if possible. In most of these methods, raw materials necessary for the reaction are fed into the reactor collectively at the beginning or only a part of the raw materials is charged continuously or intermittently during the reaction, but various reaction conditions are maintained constant. In some cases, analytical operations are carried out during a reaction. However, they are only such that the temperature and pressure of the reaction, the revolution speed of a stirrer, etc., are simply caused to vary in accordance with a schedule, or the reaction conditions are controlled according to the data obtained by converting signals from a commercially available sensor through simple processing. For example, the operation procedures are merely to detect the reaction temperature by a temperature sensor to regulate the heating level of a heater or to measure the pH of a liquid by means of a glass electrode so as to add a pH-controlling solution. The cases to which these procedures are applicable are limited entirely to those where adequate detection sensors are available and, in addition, a monitoring system, by which signals are obtained at required intervals, can be employed. In other words, due to the limitation to the monitoring system which does not require various pre- and post-treatments for an object to be treated, the reaction, which is to be conducted under the conditions adjusted according to the momentarily changing properties of a material in the reactor, had to be continued under the conditions estimated based on the past experience and the like.

Further, when analysis has to be carried out during a reaction, 1) sampling, 2) pretreatment, 3) analysis, 4) post-treatment, etc., are generally repeated generally manually. In industrial production sites, research laboratories, etc., however, it is troublesome from the standpoint of manpower to continue the daily analysis repeated at intervals of a few minutes to a few hours, and also errors are unavoidably generated by analytical personnel.

As an auxiliary means to solve these problems, so-called automatic analytical apparatus have anyhow become commercially available in recent years. For example, when set with a sample (to be exact, a receptacle containing a sample liquid having undergone a pretreatment), an automatic titration apparatus starts titration, determines the end point, and prints out the results. Generally, in the apparatus of this kind, a turntable or the like is provided as an adjunct for analyzing a large number of samples in order. However, such mechanism can only analyze, say, eight samples having undergone a pretreatment and setting, and in addition the post-treatment will also have to be dependent on manpower. Moreover, with this apparatus, it is absolutely impossible to feed back the analytical results to the operation conditions of the reactor under reaction. Furthermore, in a batch operation, the amount of the substance to be analyzed varies with the progress of the operation, and therefore the amounts of the substance and analytical reagents to obtain proper analytical results and accuracy are, in general, not irrelevant to the progress of the operation. Hence, the concentration of the substance to be analyzed in the system can vary significantly from the beginning to the end of the reaction. However, in such a case as the above-described samples, there is a serious problem that since the samples taken previously and pretreated are to be arranged on a turntable, it is substantially impossible to take samples successively and regulatively in accordance with the progress of the operation in such a way that the amounts of the samples are optimized with regard to analytical accuracy. These circumstances are exactly applicable to the aforesaid instrumental analytical apparatus including gas chromatography and liquid chromatography.

The present inventors have made intensive investigation into a method whereby tracing of the time-dependent variation of a fluid composition is made possible through high frequency analyses by automating the analytical procedures as described above, which have not been very usable, leading to completion of the present invention.

BROAD DESCRIPTION OF THE INVENTION

According to the present invention, there is provided an automatic analytical apparatus for analyzing the composition of a fluid involving a time-dependent variation of composition, which apparatus comprises:

1. at least one treating receptacle,
2. a quantitative sampling means of a fluid sample into the treating receptacle,
3. a quantitative supply means of each analytical reagent necessary for the analytical operation,
4. a pre-treatment means for subjecting the obtained sample to at least one pre-treatment operation selected from the group consisting of heating, cooling, filtration, adsorption and dissolution,
5. a detection means for detecting the analytical course,
6. a signal conversion means for converting the detected signals,
7. a discharge means for ejecting the liquid contained in the treating receptacle,
8. a means for processing the analytical course detection signals, calculating analytical results, and determining the next analytical conditions, and
9. a control means for actuating each of the foregoing means in order according to a predetermined rule, by means of which a series of operations ranging from the sampling into the treating receptacle, pretreatment, analysis and discharge of a fluid sample to the preparation of the next analysis are repeated automatically in sequence so that the time-dependent variation of the composition is traced in order, thus permitting the presence of the composition variation or the course of the composition variation to be confirmed or the composition variation to be controlled, automatically.

The present invention also provides a method for the automatic analysis of the composition of a fluid involving a time-dependent variation of composition, which method comprises:

a. preparing an analytical apparatus comprising:
1. at least one treating receptacle,
2. a quantitative sampling means of a fluid sample into the treating receptacle,
3. a quantitative supply means of each reagent necessary for the analytical operation,
4. a pre-treatment means for subjecting the obtained sample to at least one pre-treatment operation selected from the group consisting of heating, cooling, filtration, adsorption and dissolution,
5. a detection means for detecting the analytical course,
6. a signal conversion means for converting the detected signals,
7. a discharge means for ejecting the liquid contained in the treating receptacle,
8. a means for processing the analytical course detection signals, calculating analytical results, and determining the next analytical conditions, and
9. a control mean for actuating each of the foregoing means in order according to a predetermined rule, b. sampling a fluid sample into the treating receptacle,
c. pre-treating the fluid sample,
d. analyzing the pre-treated sample,
e. ejecting the fluid sample having undergone the analysis from the treating receptacle, and
f. repeating the foregoing steps b to e again automatically in order, whereby the time-dependent variation of the composition is traced sequentially, permitting the presence of the composition variation and the course of the composition variation to be confirmed or the composition variation to be controlled, automatically.

The present invention is described in detail as follows:

The fluid in the present invention signifies a gaseous or liquid mixture containing substances to be analyzed. The gaseous mixture can contain liquid droplets and powder, and the liquid mixture can contain gases and solid particles as far as they can be handled as a fluid as a whole and do not cause valves, etc., in a piping to clog. The fluid also characteristically involves a time-dependent variation of the composition.

In the present invention, a microcomputer (hereinafter referred to as "micom") is used as a means for processing detected signals in the course of analysis, calculating analytical results and determining the next analytical conditions. The micom used in the present invention is composed of a set of apparatus comprising one or more central processing circuits having arithmetic operation and data memory functions and is optionally equipped with a data display, a printer for printings and graphics, etc., which is a system having a composition capable of saving the programs for actuating these instruments. The micom by itself or in combination with a programmable controller (PC) can also be employed as a controlling means for actuating each of the above means sequentially in accordance with a predetermined rule (see below for detail). For example, personal computers having a central processing circuit of 8, 16 or 32 bits appended with input and output functions of external signals are typically used. The controlling means includes an apparatus formed as an exclusive controller by assembling the functions necessary for the apparatus of the present invention. The micom of the present invention is not influenced by the kind of programming language for its operation so that it can use any languages such as BASIC language, C-language, assembler and machine language.

There are no particular limitations placed on the quantitative sampling means of a fluid sample in the present invention. Thus, where the pressure of the fluid is higher than in the analytical receptacle, it may be utilized as a means of producing flow by the pressure. In the other cases, the sample may be transferred by means of a booster pump or evacuation mechanism or removed after being distributed into a sampling receptacle.

The treating receptacle to be subjected to analysis in the present invention can vary with various analytical procedures adopted, and it is preferable to chose a material suitable for the analytical procedure among proper materials such as glass, quartz, stainless steel, or porcelain. Particularly, where analysis is conducted by an optical means from the outside of the receptacle, receptacles of cell structure made of glass or quartz are preferred, while when heating or cooling of a sample is required upon analysis, those of quartz, stainless steel or porcelain are suitable. Where the influence of water, oxygen and nitrogen in the air has to be prevented in view of the characters of the analytical procedure, it is advisable that the receptacle be hermetically sealed and communicated with the air through a drying tube or charged separately with an inert gas.

DETAILED DESCRIPTION OF THE INVENTION

Figure 1:
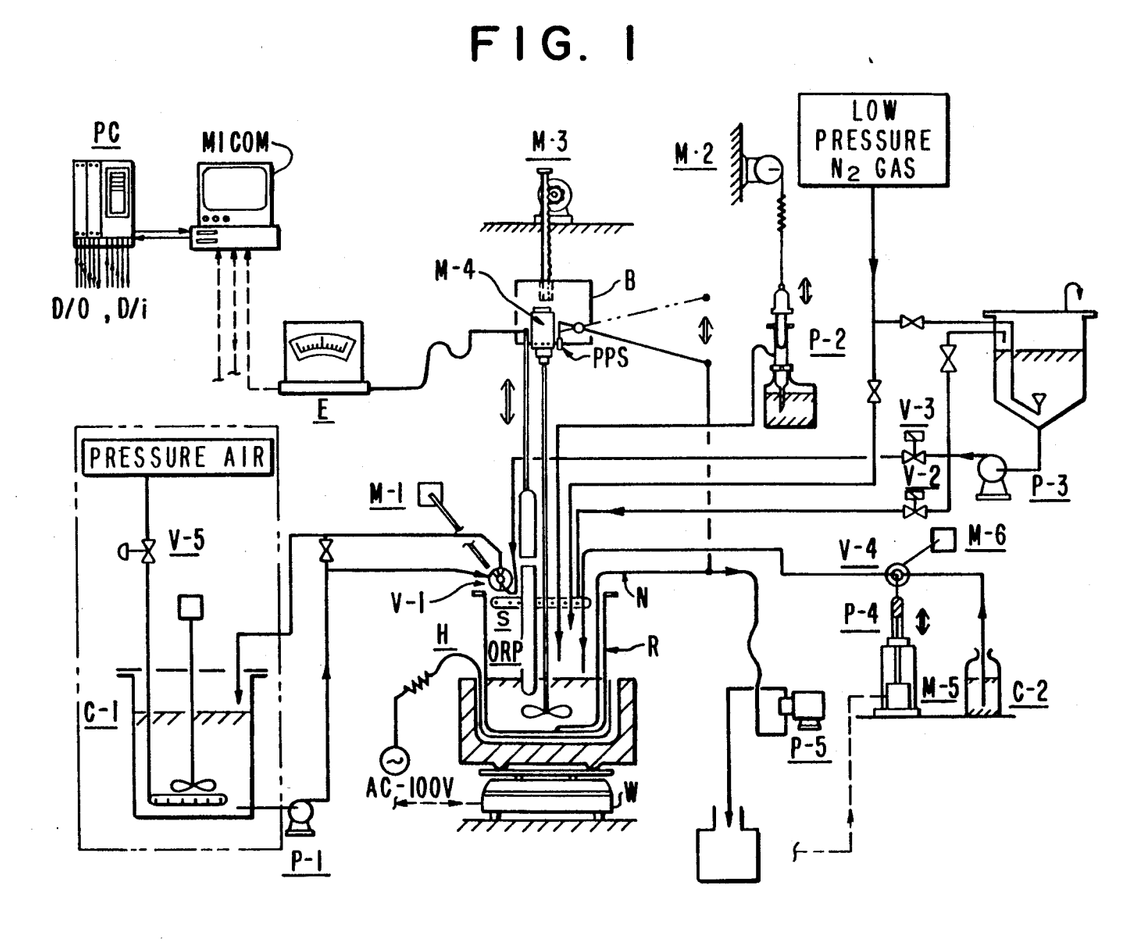
FIG. 1 is a drawing illustrating a flow diagram of the apparatus suitable for putting the invention into practice.
Figure 2:
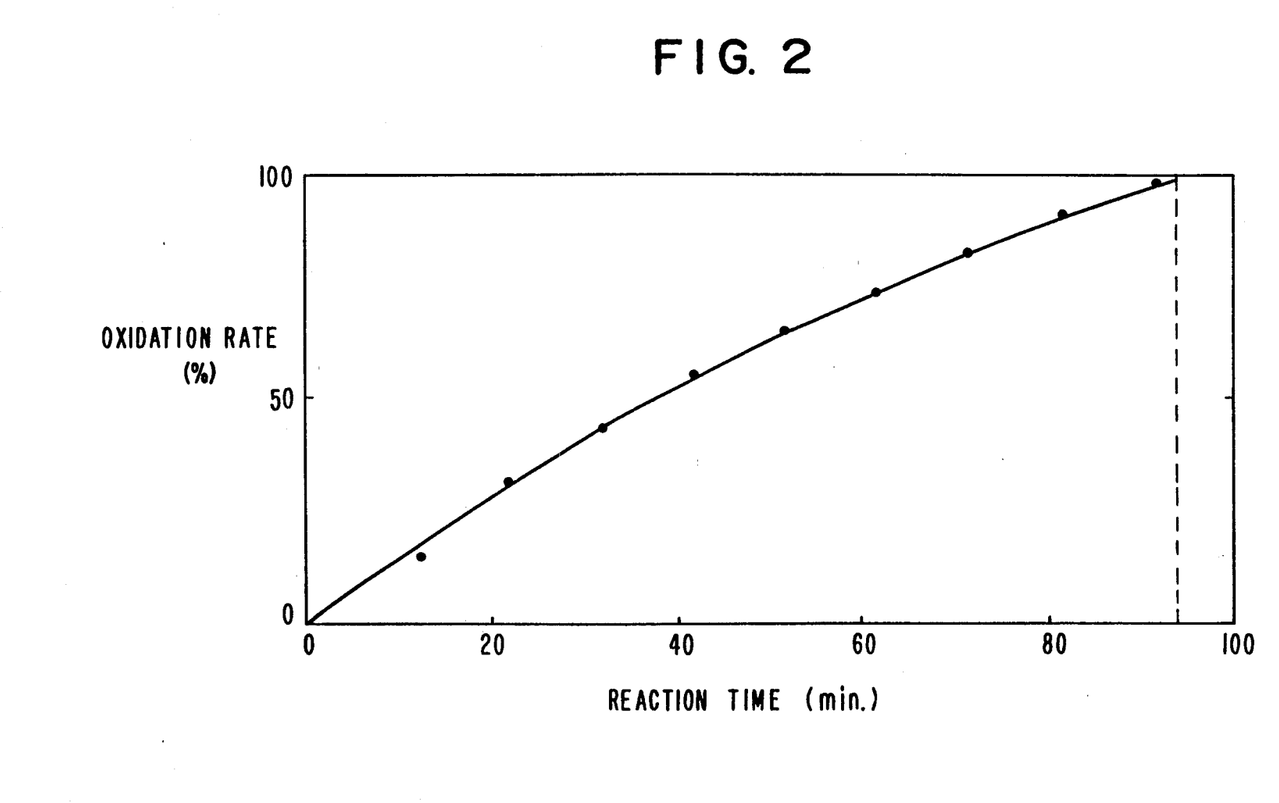
FIGS. 2 and 3 are graphs showing the relationship between the rate of oxidation and the reaction time.
Figure 3:
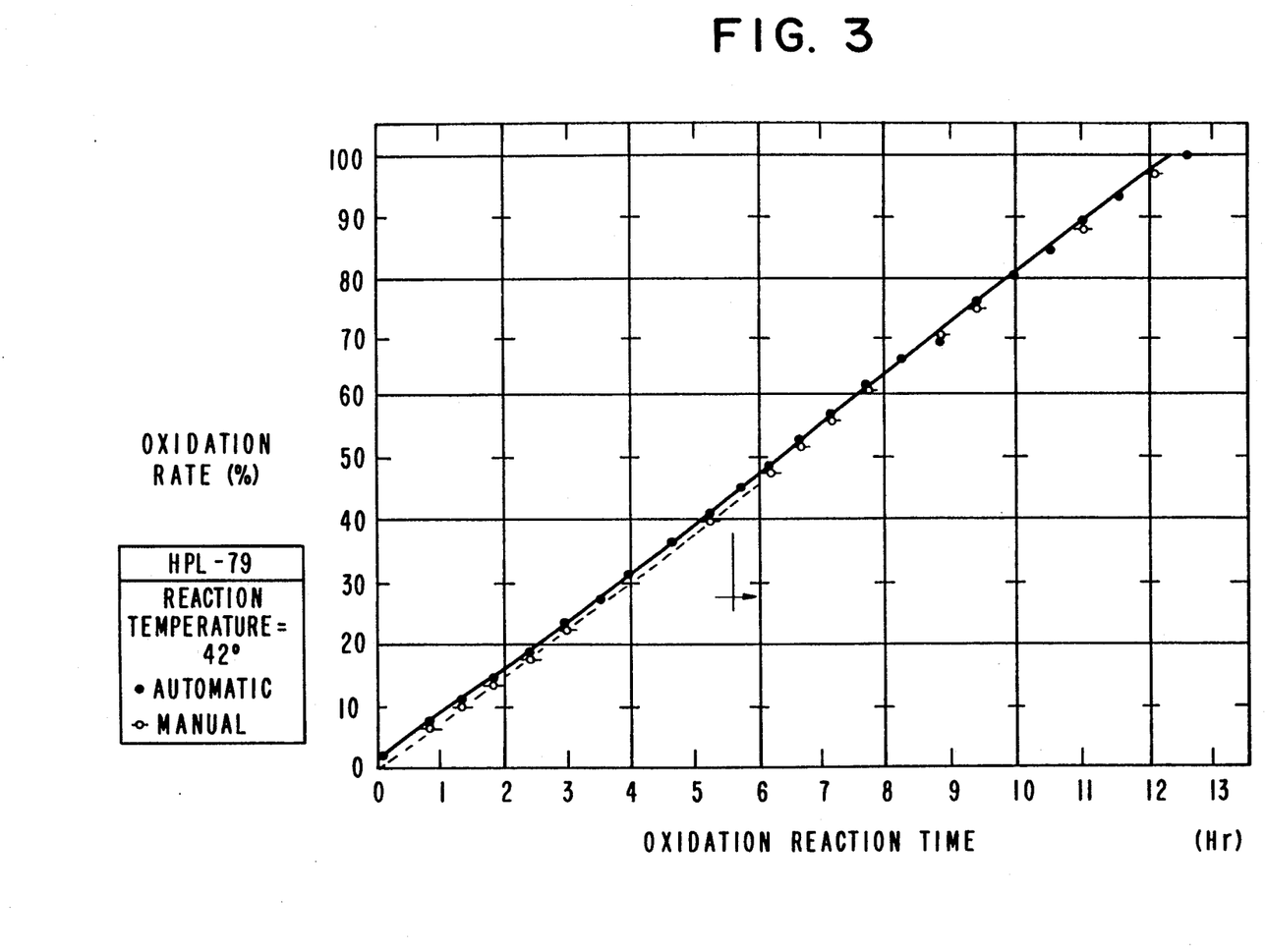

In FIGS. 1 to 3, C-1 is receptacle, C-2 is brown standard solution bottle, D/i is each input signal, D/0 is each output signal, E is potentiometer, H is heater, M-1 is valve-switching low speed motor, M-2 is rotary solenoid, M-3 is up-and-down geared motor, M-4 is stirrer motor, M-5 is pulse motor, M-6 is 3-way cock switching motor, N is suction nozzle, P-1 is external recycle pump, P-2 is commercial dispenser, P-3 is water recycle pump, P-4 is cylinder pump, P-5 is waste water gear pump, PC is sequencer, PPS is push-pull solenoid, ORP is oxidation-reduction electrode, R is treating receptacle (beaker), S is porous ring (shower ring), V-1 is 3-way rotary cock, V-2 is feed water electromagnetic valve, V-3 is washing water electromagnetic valve, V-4 is 3-way cock, V-5 is gas volume control valve, and W is precision balance.

Figure 4:
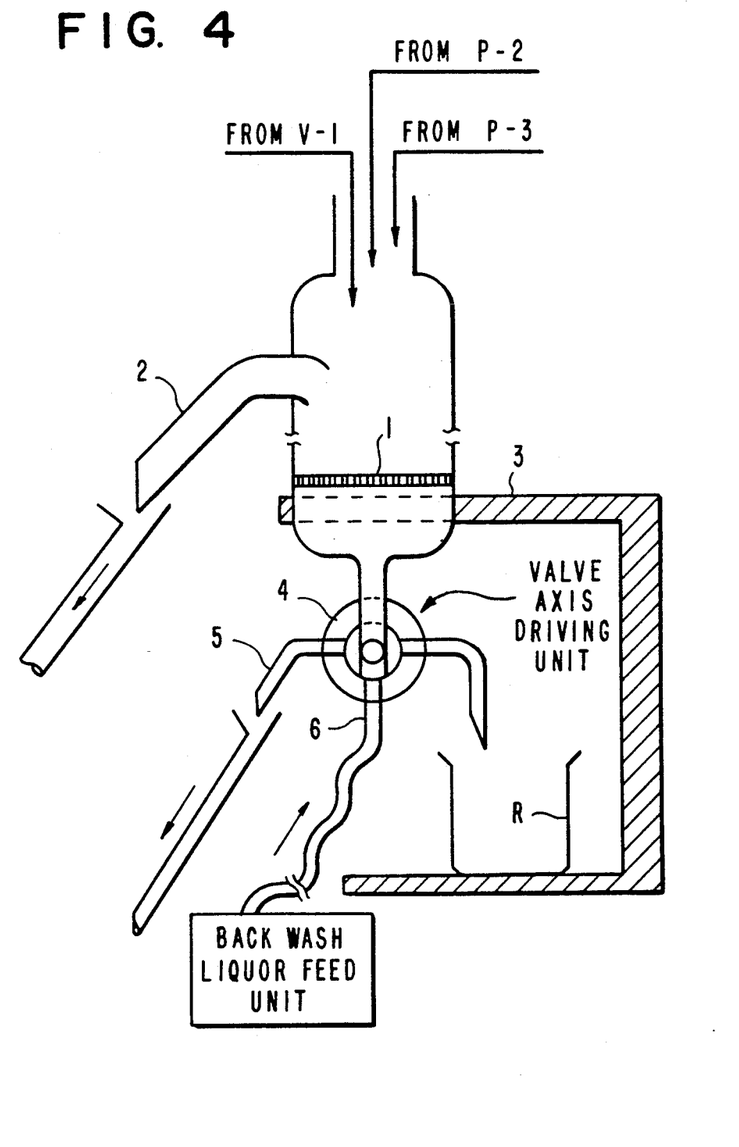
FIG. 4 is a drawing illustrating a filtration apparatus for carrying out filtration operation as a pretreatment in the invention.

In FIG. 4, the numeral 1 is a filter, the numeral 2 is a back wash liquor discharge nozzle, the numeral 3 is a weighing frame, the numeral 4 is a 3-way select valve, the numeral 5 is a waste liquor discharge nozzle, and the numeral 6 is a back wash liquor feed nozzle.

Figure 5:
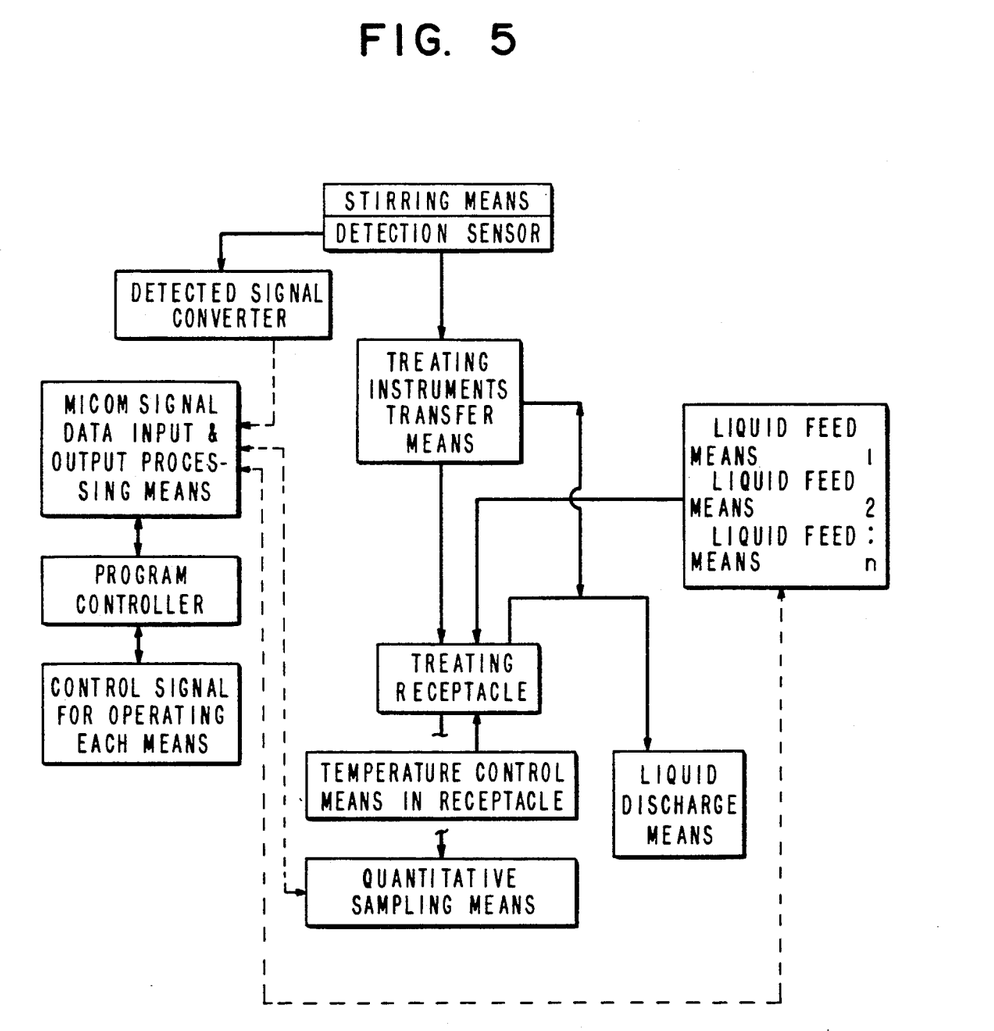
FIGS. 5 and 6 are block diagrams illustrating the operations of the present invention.
Figure 6:
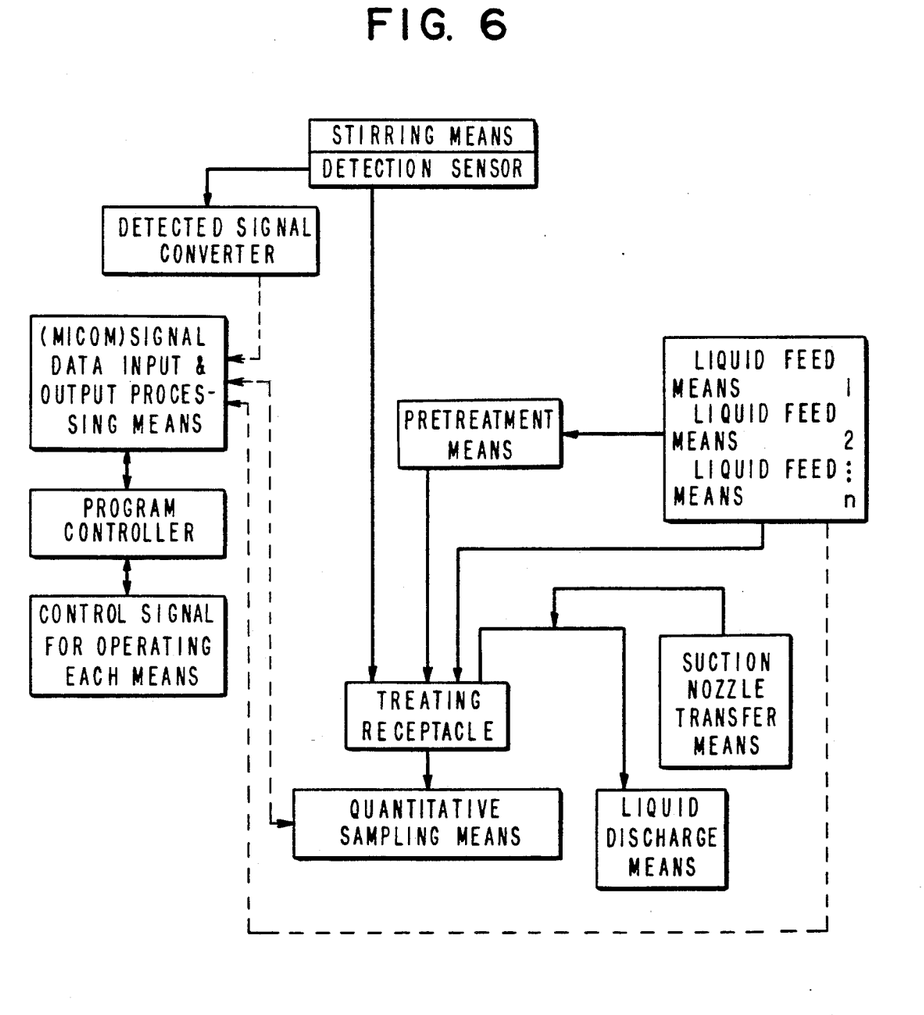

In FIGS. 5 and 6, the dotted lines show flows of signals.

In the analytical apparatus of the present invention, the above treating receptacle may preferably be equipped with all components necessary for the analysis. Examples of such components may include, as shown in FIG. 1, a balance provided with a communication function for weighing the amounts of a sample and other additives by placing the above treating receptacle thereon or hanging the same therefrom; a medium-circulating jacket, hot plate or electric heater for cooling or heating the sample for its pretreatment as required; an insulating device for this purpose, an agitator for the liquid in the receptacle, various electrodes as described below, a nozzle for charging additives, a nozzle or perforated ring for washing these components in the receptacle after completion of each operation, a liquid discharge nozzle, etc. The receptacle is also provided with a quantitative supply means of individual analytical reagents necessary for the analytical operation.

In the present invention, it is most effective in principle that all of these components are installed for one treating receptacle. However, when the time required for the series of steps from sampling, pre-treatment, analysis to post-treatment is longer than the time interval during which the analytical result is needed, or when functional restrictions can be eliminated by a proper arrangement of the above components, two receptacles may be used, one for the steps up to the pre-treatment and one for those from the analysis onward by way of example. In this case, the transfer of a sample having undergone the pre-treatment to the side of analysis is effected by causing the sample to move to a second washed receptacle by gravity or by exchanging the receptacles mechanically. In the former case, accuracy is improved by washing attached matters with a liquid not affecting the analysis and adding the washings to the liquid to be analyzed. However, the latter procedure is more accurate. By letting the treating receptacle and components have mechanisms which can automate all the steps up to the post-treatment such as washing, the measurement can be continued without being substantially affected by the number of times of analysis. In the present invention, there is provided a pre-treatment means for subjecting an obtained sample to at least one pre-treatment operation selected from the group consisting of heating, cooling, filtration, adsorption and dissolution.

The heating, cooling or dissolution as a pre-treatment operation of an analytical sample may be effected as demonstrated in the examples below, and hence it may not require any particular explanation. Therefore, the filtration and adsorption will be illustrated hereunder. The filtration itself may be carried out by an ordinary method in which solid components in a sample are separated by a filter adaptable to the solids, and the attached solution is washed with a washing agent. When the filtrate is to be analyzed, it is introduced into a treating receptacle. Specifically to the apparatus of the present invention, the quantity of a sample is determined precisely in an automatic way and, to ensure a smooth continuation of the repeated operations, the solid components are removed automatically from the filter at given intervals. The quantitative and automatic sampling of a sample is effected (1) by controlling the operation duration of a quantitative feed pump or (2) by measuring the weights of the sample plus the filter and the receptacle collectively. Further, the removal of the solid components from the filter is carried out (1) by dissolving and removing the solids with a solution having a composition capable of dissolution thereof or (2) by injecting a washing agent from a 3-way branched valve unit under the filter to the back side of the filter so as to back-wash and remove the solid components. When the solid components are to be analyzed, the above-described dissolved solution is introduced into the receptacle. The apparatus for the filtration method is illustrated in FIG. 4.

Numeral 1 indicates a filter provided with a back-wash liquor feed unit under a 3-way select valve and with a valve-stem driving unit for actuating the valve. R is a treating receptacle.

As a pretreatment operation of an analytical sample in the present invention, it is possible to use a lengthwise-long adsorption column having the shape similar to the component shown in FIG. 4. In other words, the filter 1 in FIG. 4 is made to provide pores having diameters adapted to the grain sizes of an adsorbent, and then the adsorbent suitable for the sample pretreatment is packed in the column to prepare an adsorption column. The adsorption is effected (a) by adsorbing components that obstruct the analysis and introducing components to be analyzed into a treating receptacle or (b) by adsorbing components to be analyzed, discharging the obstructing components from the discharge nozzle of the 3-way select valve and, after a washing agent is used to wash the adsorbent and discarded when perfection is aimed, changing the discharge nozzle of the 3-way select valve to the side of the treating receptacle R so that the eluate of the adsorbed components is poured into the receptacle for analysis. Depending on the natures of the adsorbent and the sample, it may be necessary to back-wash the adsorbent itself after several times of sample feed. In this case, it is possible to back-wash the adsorbent by operating a back-wash liquor injection unit in accordance with a given schedule.

The adsorbent packed in the adsorption column used as a component of the apparatus of the present invention may include ion-exchange resins, active carbon, alumina-silica granules, synthetic zeolite, hydroxyapatite, chemically-bonded silica gels, porous polymers, etc.

In the present invention, there is provided a discharge means for discharging a liquid having undergone an analysis and contained in the treating receptacle, which may, for example, be a suction nozzle in which the discharge nozzle of washing wastes in at least one receptacle is driven by an up-and-down driving mechanism mounted above the receptacle in the above automatic analytical apparatus.

As a general mechanism for discharging liquids from a receptacle, the discharge through a nozzle by opening and closing a valve is often used, including tank valves having the structure in which the valve face is in continuous agreement with the inner surface of the receptacle to prevent liquids from gathering in the valve section. However, when such valve structures are adopted, liquid gathering, biting solids at the opening and closing section, and abrasion are inevitably caused and, depending on the analytical procedure employed, the apparatus may not be achieved in most cases due to the limitations on the valve material such as its heat resistance, chemical resistance, and thermal shock on heating or cooling. The present inventors have made intensive investigations to overcome these conditions and finally found that the discharge of washing wastes from the above receptacle is best performed by lowering a suction nozzle only when needed. No particular restrictions are imposed on the driving source for this purpose, and an air cylinder, electric motor, or a push-pull or rotary solenoid may preferably be employed by way of example.

In the present invention, upon sampling of a sample of a material to be analyzed, whose concentration varies with time, the amount of the obtained sample can also be automatically varied so that the amount of the material to be analyzed in the sample may be varied by referring to the analytical result of the last sample.

The determination of the amount of a sample may be based on either volume or weight and can also be corrected by the function of the micon using the inherent specific gravity of the sample. A desirable example gives, as shown in FIG. 1, such a scheme that a fluid in a reactor C-1 of various kinds or a still is withdrawn and circulated by a pump P-1, a motor- or air-driven 3-way rotary cock V-1 is provided on the exit line of the pump, one of the outlets of the cock is communicated to a treating receptacle R on a balance, the amount of the obtained sample is measured by the communication between the micom and the balance W, and the cock is changed over when a predetermined amount is attained. This is an example of the quantitative sampling means of a fluid sample to a treating receptacle. The amounts of the obtained samples are selected according to the material to be analyzed and its analytical procedure, the characteristics of reagents such as concentration and detection limit, and the varied amounts of the material to be analyzed with the progress of the reaction, and it may be advisable to control the maximum sampling amount to be 30 times or less, preferably 10 times or less, of its minimum sampling amount, depending on the time required for the instruments to perform a pre-analytical treatment, analysis and post-treatment and their capabilities including capacities. When these sampling amounts are identical, the amount of each reagent has to be changed properly. However, when the concentration of the material being analyzed varies from 100 percent to 1 percent by way of example, it is difficult to maintain an effective analytical precision over a wide analytical range. For the same reason, it is unfavorable for the sampling amount to exceed the 30 times from the standpoint of maintaining the analytical precision owing to the limited operational capabilities of the individual components.

The amount of the first sample is estimated by man and stored in the micom to initiate analysis. Though depending on the analytical procedure employed, it may happen that adequate analyses may not be performed in such an extreme case as the concentration of the object being 0 percent or 100 percent. To cope with this case, it is possible to allow the micron to estimate the end point extrapolatively from the past analytical values. Further, in the present invention, there is provided a quantitative supply means of analytical reagents necessary for the analytical operation.

In the present invention, it is also possible to change the initial feed rate and/or feed amount of an analytical reagent by referring to the analytical result of the last sample and the present sampling amount.

When the sampling amount of the present analytical sample is changed in accordance with the progress of the reaction or distillation by referring to the last analytical value, the amount of each reagent necessary for the analysis is varied. If the initial addition rate of the reagent is kept unchanged in spite of this variation, an unexpectedly long time is required and errors are caused in the analytical result itself. For the total amount of each reagent required for one analysis, it may also become necessary to add its greater part quickly and feed the rest slowly. In the case of the apparatus of the present invention, such analytical conditions may automatically be changed in order by referring to the last analytical value and seeing the progress of the variation by the functions of the micom. In the present invention, a sensor is used as a means for detecting the analytical course.

In the present invention, it is also possible to employ the methods of colorimetric analysis for inorganic ions and the absortiometric methods by ultraviolet, infrared or visible radiation as the analytical procedure.

The colorimetric methods, including the fluorescent colorimetric method, determine colorimetrically the density of a color produced by a coloring reagent suitable for ions to be analyzed by the use of a photo-electric converter such as a photo-electric photometer, in which any interfering elements present in the sample should be removed by a pretreatment such as precipitation-filtration. The analysis can be repeated by dissolving the precipitate followed by washing in the post-treatment. The absorptiometric methods are those commonly employed in analytical chemistry, which determine quantitatively a component to be analyzed by allowing a light formed by spectral separation and having an absorption wave length specific to the component to transmit through the sample after a pretreatment and measuring the quantity of the light. In the apparatus, the light for analysis is irradiated and received in such a way that the irradiation and the reception are conducted on the outsides of an analytical receptacle made of glass or quartz, or the irradiated light is introduced into a sample under analysis using a glass fiber bundle or glass rod and the transmitted light at a certain distance is received in the same manner. It is preferable to use quartz as the material for ultraviolet radiation.

In the present invention, various methods including the analytical method may also be any one of the following: potentiometric titration method, photometric titration method and polarization titration method, including those of neutralization titration, oxidation-reduction titration, precipitation titration, chelatometric titration and colloidal titration, regardless of whether the system is aqueous or nonaqueous.

In the potentiometric titration method, a differential electromotive force produced in a liquid is measured from the outside using commercially available electrodes such as glass electrode, platinum electrodes and reference electrodes, and it is common practice to use electrodes yielding outputs which can be read out by the micom. However, the method is not limited to these commercial electrodes so far as it can measure the composition variation of a component to be analyzed involved in titration operation as a change of potential. The photometric titration method detects the end point of titration by the change of the light quantity or color of a transmitted light and hence may use the same optical system as employed in the aforesaid colorimetric and absorptiometric methods. In the polarization titration method, various electrodes can be selected, and there is such a method in which a calomel electrode and a dropping mercury electrode or rotary platinum microelectrode are used and a method in which a certain minute voltage is applied between two microelectrodes of the same kind such as of platinum to measure the change of current caused by titration and determine the equivalence point. Further, in the present invention, there is provided a signal conversion means for converting signals detected by a sensor to electric signals.

In the present invention, the samples used may also be those obtained from the reaction solution in which goethite particles are formed by oxidizing, with an oxidizing gas, the suspension of hydroxides obtained by reacting an aqueous solution of a ferrous salt with an aqueous solution of an alkali.

The analytical apparatus and method of the present invention may favorably be applied to the production process of goethite particles, but are not limited thereto as a matter of course.

The goethite particles obtained to date by the above reactions are used as coating pigments. In addition, they are subjected to various subsequent processes, for example, are reduced to iron particles so as to be used as magnetic pigments for magnetic recording media and as raw materials for various ferrite products and electric wave absorbers. Goethite particles have conventionally been produced by stirring the above aqueous solutions fed to a tank at a given proportion, injecting air thereto at a given feed rate to conduct the oxidation reaction, and taking the resulting particles out after a given period of time. In this process, many trails and the accumulation of operational experience have been required in order to modify the characters of the particles such as shape and to obtain reproducible products. Further, to grasp the reaction conditions, it has been necessary to make samples and analyze the metallic ions through titration by man, which requires an extremely complicated pretreatment. Hence, once the reaction is started, it is performed automatically. Thus it is carried out almost under a so-called blind state of operation only maintaining the conditions, and only the confirmation of the end point, at which the oxidation-reduction potential is changed rapidly when the oxidation reaction is complete.

The present inventors have made intensive investigations into the process for producing these particles and finally found that to improve the characters of the particles which exert great influence on the properties of the products for the aforementioned applications, it is essential to control the progress of the above reactions, and it becomes possible to improve the characters of the particles by modifying the time-dependent course of the progress.

Then a conclusion is reached that it is impossible to perform this modification reproducibly only by the confirmation of the end point, and to this end, it is inevitable to conduct frequent analyses for tracing the course of the reaction progress and to control the reaction conditions on the basis of the analyses. Thus, various analytical means and apparatus are investigated, leading to completion of the present invention.

As an embodiment of the present invention, where the invention is applied to the production of goethite particles, a sample is taken automatically from a tank in which goethite particles are being produced, and since the sample under the reaction is a suspension of iron hydroxides and goethite particles, pretreatment operations such as dissolution of the particles and subsequent dilution are preformed entirely automatically. Then, the amount of the unreacted ferrous ions present is automatically titrated using a standard potassium permanganate solution (hereinafter simply referred to as the standard solution), and the change of the oxidation-reduction potential is stored and data-processed by the micom, thereby performing sequential analyses. Further, because all components after completion of one analysis are washed automatically, preferably one, at most receptacles are used in the pretreatment and analysis, and the amount of the obtained sample and/or at least one of the initial feed rate and feed amount of a feed reagent are automatically changed referring to the last analytical result and the sample amount.

An embodiment of the present invention will be described hereunder with reference to FIG. 1. Needless to say, the present invention is not limited to or by such an embodiment. It is a matter of course that, for example, the kinds of the individual components are not limited to those described below and may hence include those constituting a mechanism having the same operational function.

In the present invention, a branched line from the line through which the contents in a tank C-1 under the above reaction are externally circulated is first connected to an automatic 3-way rotary cock V-1 so as to open the sampling side by a micom signal, so that a sample is taken in a beaker R-1, the treating receptacle. The beaker is on a precision balance W and the weighed values are communicated to the micom every moment. When a predetermined weight is attained, the above cock is closed and the weight is measured again precisely. In the present invention, a quantitative supply means of each analytical reagent necessary for the analytical operation is provided. In this case, concentrated sulfuric acid, an analytical reagent added into the beaker for dissolution of the particles, is first sucked by raising the piston of a commercial glass dispenser P-2 by the torque of a rotary solenoid operated by a micom signal and then fed into the beaker by gravity after release of the solenoid. In general, there are many procedure of feeding a given amount of an analytical reagent into a treating receptacle for the purpose of analysis. If the amount of a reagent does not require such exactness, a so-called quantitative pump of piston or tube type may also be used. When the reagent is corrosive, the wetted part of the pump should preferably be of glass as described above, stainless steel, ceramics and fluororesisn (e.g., teflon) are also usable.

The beaker, placed in a cylinder made of a heat insulating material, is heated by a heater H controlled in heating time by the micom, so that the particles are dissolved at a high temperature. The heating-dissolution is one of the pretreatments of the present invention. Upon completion of the heating, an electromagnetic valve controlled by the micom is opened to pour dilution water, having had dissolved oxygen removed by low pressure $N_2$ gas, oxygen, into the beaker for a predetermined period of time. The above is the pretreatment step.

For the analysis of the sample pretreated as described above, a stirring blade and a platinum electrode for titration, both of which are mounted on a board B moving between predetermined heights by a motor M-3 operated by the micom, are lowered into the sample solution, and the electrode potential is continuously read by the micom with the aid of a potentiometer E while stirring the solution.

The above standard solution is stored in a brown standard solution bottle C-2 and is fed in a cylinder pump P-4 of piston type pushed by the thrust of a ball screw connected to the axis of a pulse motor M-5, which is controlled in rotating speed by the pulse delivered from the micom according to program conditions. The solution is then fed precisely into the beaker by the pump actuated by the micom so as to conduct a titration. In the titration, the oxidation rate based on the last analytical value is divided preferably into less than 50 percent, between 50 percent and 80 percent, between 80 percent and 90 percent, between 90 percent and 97 percent, and more than 97 percent by way of example, so that the feed rate and time of the standard solution and the waiting time for stabilizing the potential are changed correspondingly, and the potential change (dE) vs. the amount of the solution fed (dV) are calculated for each measurement of the potential. Upon the specific variable calculated using these data reaching a given value, the feed conditions are changed in order and thus turning point of the titration curve, i.e., the end point is determined in the conventional manner. Using the amount of the standard solution fed, the micom calculates the amount of ferrous ions, the rate of oxidation, etc. For example, when the present rate of oxidation is 97 percent, the amount of the next sample is increased by a predetermined ratio and the feed of the standard solution is started at a minimum prescribed rate.

Upon completion of the titration, the automatic 3-way cock V-4 at the outlet of the cylindi pump P-4 is changed to the suction side and the pump piston is lowered to let the standard solution in by a signal of the micom.

On the other hand, the above electromagnetic valve for dilution water, which is led to a shower ring S with a number of downward pores installed along the inner walls at the upper part of the beaker, is opened to start washing inside the beaker. At the same time, a push-pull solenoid PPS, the up-and-down driving mechanism joined to the above moving board B, is actuated by a micom signal, so that a suction nozzle N for waste liquor provided at the tip thereof is inserted all of the way to the bottom of the beaker and a waste liquor pump P-5 is operated to discharge waste water. After a given period of time following closure of the electromagnetic valve for dilution water, the waste liquor pump is turned off.

Then, the waste liquor nozzle is raised by actuation of the solenoid, i.e., the up-and-down driving mechanism, and the above moving board is also lifted to the initial position, thereby keeping the electrode and the stirrer above the beaker.

One cycle for the series of operations for repeating the analysis is as described above. It is, however, entirely included in the scope of the present invention to add such functions as turning the heater on again to dry the beaker after washing, blowing nitrogen gas with a view to isolating the air above the heater, putting the beaker and its adjunct in a nitrogen box, varying and controlling the heater voltage or heating time, modifying the initial feed condition of the standard solution in view of the actual conditions of analytical objects and procedures.

FIGS. 5 and 6 are block diagrams showing the operations of the present invention. No detailed explanations would be necessary, but FIG. 5 shows the case where a means for controlling the temperature of a treating receptacle is also provided, while FIG. 6 illustrates the case where no temperature control is required.

BEST MODE FOR PRACTICING THE INVENTION

Preferred embodiments of the present invention will be specifically described as follows with reference to the following examples. It should, however, be understood that each of the examples in the description is only an illustration of the method and apparatus for practicing the present invention and is not at all a limitation on the scope of the present invention. It goes without saying that components constituting a mechanism with the same operational function are included in the technical scope of the present invention.

EXAMPLE 1

FIG. 1 is an illustration of the application of the present invention to the production of goethite particles, showing a situation under titration analysis. The operation is carried out according to the block diagram given in FIG. 5.

Into a 100-l stainless steel receptacle with a stirrer (C-1 in FIG. 1) containing 56 l of an aqueous sodium hydroxide solution (concentration: 2.75 mol/l), which had been removed with dissolved oxygen in advance by nitrogen gas bubbling, was fed 24 l of an aqueous solution of ferrous sulfate heptahydrate (concentration: 1.13 mol/l) by a pump. A valve V-5 was opened to introduce air under pressure through a ring sparger at the bottom of C-1, thus starting the production of goethite particles under continued stirring. The temperature of the suspension under the reaction was maintained at 35° C., while the amount of the air was kept at 720 l/hr. The oxidation reaction took about 95 minutes for completion, during which samples of the reaction liquid were taken, pretreated and analyzed automatically and repeatedly according to the schedule set previously to ensure than no abnormal reactions were taking place.

In FIG. 1, the section surrounded by the chain line and situated on the left side of a sampling pump P-1 shows an example of the apparatus for producing "fluid" of the present invention PC in the drawing signifies a common program controller (referred to as sequencer alternatively), which has fundamental functions capable of delivering signals for actuating external electronic instruments according to a program, or, contrariwise, receiving external signals and delivering them after a predetermined time by its timer function, or grasping the present situations of the delivery and reception of signals by its memory function. The micom in the present invention also has these functions, but since the micom in this example performs repeated measurements of an electrode potential, repeated feed of a titration standard solution by the control of a cylinder pump, and repeated numerical calculations based on the data obtained and repeated judgments of their results, simple operations are instructed by the PC, the program of which is actuated each time by the micom.

In FIG. 1, there is no particular illustration of known detecting instrument, such as doubly installed photosensors and limit switch, for detecting the hang-up position of driving parts and for safety purposes.

In Example 1, the liquor in the receptacle C-1 is analyzed prior to the introduction of air under pressure to provide the first datum. The subsequent data are all taken in the course of the oxidation reaction under the introduction of air. The liquor in the receptacle C-1 is always circulated externally by an external recycle pump P-1. A motor M-1 is rotated and stopped at a predetermined position by the digital signal (hereinafter abbreviated as D/O) delivered according to a program in the PC that is started by an actuation signal of the micom. Thus, the liquor flows through a 3-way rotary cock V-1 into a beaker R, which is treating receptacle with a volume of 200 ml, i.e. the analytical receptacle. The beaker R is placed on a precision balance W, with an electric heater H and a heat insulator between them. The weighed values by the balance W are transmitted every moment to the micom.

When the preselected weighed value (about 3 g in the beginning) is attained, the micom instructs the PC to deliver a D/O to rotate the M-1 by 180° so that the cock V-1 is connected to the external circulation. The micom stores the sample amount weighed precisely.

To dissolve the particles in the sample, the micom instructs the PC to deliver a D/O to turn a rotary solenoid M-2 so that a commercial dispenser P-2 sucks concentrated sulfuric acid, and then to return the M-2 after a preset period of time so that the piston of the M-2 descends and thus the concentrated sulfuric acid in a preset amount of 10 cc is fed in the receptacle R. Subsequently, the heater H is turned on by the PC for a certain period of time, during which the particles in the samples are dissolved.

In FIG. 1, P-3 is a dump for circulating dilution water having had dissolved oxygen removed by low pressure $N_2$ gas. After turning the heater H off, the PC transmits a D/O to open a 2-way electromagnetic valve V-2 for a certain time and thereby feed about 50 ml of the dilution water into the beaker R to dilute the sample. Simultaneously with closure of the V-2, the D/O drives a geared motor M-3 to cause a stirrer with a motor M-4, a platinum electrode (ORP), etc., to descend (these are, as shown in the drawing, mounted on the board B and move vertically as one body).

By means of a photosensor for detecting position, not shown in the drawing, the PC confirms that the stirring blade has reached a predetermined position, then turns the M-3 off and actuates the M-4 to start stirring the liquor.

At this moment, the PC communicates the initiation of the reading of the output (i.e., the measured value of ORP) of a potentiometer E, whose electric source has been turned on, by a D/O to the micom. Thereafter, titration is started, and the operation until its completion is directed by the micom.

The standard titration solution is 1/10N potassium permanganate stored in a brown bottle C-2, and is fed in a cylindi pump (P-4) of piston type via a 3-way switch cock V-4. The pump P-4 can deliver 1.66 $\mu$l of the solution for each pulse by the movement of the piston for a certain distance owing to the thrust of a ball screw connected to the axis of a pulse motor M-5, which rotates each time a certain angle according to a pulse signal transmitted from the micom.

On titration, the micom refers to the last analytical value or the reaction oxidation rate in percentages entered prior to the initiation of the measurement. For example, when the sample is found to have an oxidation rate of 97 percent or more, the feed rate of the standard solution is set at 5 pulses per second, and the operations of feeding for a second, waiting for 5 seconds and then measuring the potential of ORP are repeated. On and after the third operation, the micom invariably computers the differential $dE/dV$ in each operation from the potential change $dE$ vs. the amount of the solution fed $dV$ for each operation, and further computes its differential $d_2E/dV^2$ (the operation from the feeding of the solution to the second order differential computation will be referred to as A 1).

In the case of the above reference oxidation rate being less than 97 percent, if it is 50 percent or more the measured potential is 570 mV or, more, the same operation as in the above operation A 1 is repeated except that only the solution feed rate is changed to 125 pulses per second (this operation will be referred to as A 2). Where the reference values are less than 50 percent and less than 570 mV, the operation A 1 is repeated by changing the feed rate to 300 pulses per second and the waiting time to 3 seconds (this operation is called A 3). Where the titration is started with the operation A 3, the operation A 2 is conducted repeatedly when the ORP potential reaches 570 mV. When the ORP potential attains 600 mV in the course of the operation A 2, feeding of the solution is stopped for 10 seconds. Then, the operation A 1 is repeated except that only the solution feed rate is changed to 10 pulses per second when the reference oxidation rate is 90 percent or more, or to 45 pulses per second when it is less than 90 percent and not less than 70 percent.

When the calculated value of $dE/dV$ exceeds 400 mV/ml in all of these operations, the operation is switched to A 1. Since the second order differential $d_2E/dV^2$ changes from positive to negative during the operation A 1, the amount of the standard solution required up to the titration end point is determined from the cumulative value of feed pulses until that point; the amount of ferrous irons in the titrated sample is then determined in the conventional manner; the difference between the amount of ferrous ions and the amount of the iron initially added is taken as the amount of ferric iron, and thus the micom computes the oxidation rate.

After calculation of the titration results, the PC starts to operate the post treatment of analysis by a D/O of the micom. Specifically, the motor M-6 is turned on so that the 3-way cock V-4 is switched to communicate the P-4 to the C-2. At the same time, a water recycle pump P-3 is actuated, a feed water electromagnetic valve V-2 is opened for 5 seconds, and then a washing water electromagnetic valve V-3 is opened and closed two times for 10 seconds each so that the sampling nozzle of the 3-way cock V-1 is washed with water. Simultaneously with the closure of the V-2, the push-pull solenois PPS is operated so as to place a suction nozzle (waste water nozzle) N, which has been held at the upper part of the beaker, on the bottom thereof and also to actuate a waste water gear pump P-5 to discharge the contents of the beaker. Switching of the 3-way cock V-4 is completed when a photosensor, not shown in the drawing, detects a notching of a disc mounted onto the axis of the motor M-6, and the PC having received the signal communicates it to the micom, which reverses the pulse motor M-5 to suck the standard solution in the brown standard solution bottle C-2 into the cylinder pump P-4 for storage. Upon closure of the valve V-3, the valve V-2 is opened for 20 seconds, and after its closure, the pump P-3 is stopped and the heater H is turned on for 120 seconds. During this time, the stirrer motor M-4 is stopped, the push-pull solenoid PPS is turned off to raise the waste water nozzle, the pump P-5 is stopped, and the motor M-3 is reversed to raise the motor M-4, push-pull solenoid PPS and oxidation reduction electrode ORP above the beaker. A series of analytical operations are completed by the above operations.

For the next analysis an external time arranged in advance communicates the actuation timing to the micom after a preset period of time. In this example, the repeated analyses are concluded when a man inputs the end from the keyboard.

The micom puts a variety of analytical results into prints in order, by means of a printer in terms of numerics and graphs. The sampling amount was about 15 g in the 10th automatic analysis.

The variation of the oxidation rate in the reaction was traced and the results are shown in FIG. 2. The cycle of the automatic analysis was 10 minutes.

Incidentally, when a man tried to repeat the analysis within the same period of time, he needed considerable skill. Further, once he failed in titration, he would no longer have enough time to repeat it.

EXAMPLE 2

Operation is carried out according to the block diagram shown in FIG. 5.

In the same apparatus as in Example 1, after exchange of the control valve V-5 to that of a proper flow range, the aqueous solution of ferrous sulfate heptahydrate was set in concentration at 0.75 mol/l, with the aqueous sodium hydroxide solution at 2.79 mol/l, and they mixed together. Then, the oxygen reduced in pressure from a high purity oxygen bomb which was blown into the C-1 at a rate of 8 l in terms of the volume at standard temperature and pressure (0° C. 1 atm.) to start the reaction, and the variation of the oxidation rate in the reaction was traced according to the automatic analysis. In this connection, with the aim of maintaining the variation of the oxidation rate constant against the reaction time, the micom delivered a control output signal according to the operational expression stored in the micom depending on the deviation between the expected oxidation rate and the actual analytical result at a given time, so that the control valve V-5 was operated so as to change the amount of oxygen gradually. The variation of the oxidation rate in the reaction was traced over 12 hours and the results are given in FIG. 3.

For comparison, the same samples were analyzed manually. The analyst had to take turns after 5 and one-half hours of the reaction. In the case of manual analysis, the end point was determined by an analyst through visual observation according to the color reaction of a potassium permagnate standard solution. FIG. 3 also shows the results. The error was large in the beginning and within 2 percent, and in the latter half of the reaction, the both values were in agreement with each other within 0.6 percent. Thus, the variation of the oxidation rate could be maintained at a constant rate.

EXAMPLE 3

Operation was carried out according to the block diagram shown in FIG. 6.

In the reaction of Example 2, the ferrous component in the sodium hydroxide solution is a white precipitate represented by the formula $Fe(OH)_2$. Following the progress of the oxidation reaction, it turns into needle crystals consisting of the ferric component. As a method to analyze the residual rate of the ferrous component in the sample in order to trace the time-dependent variation of the reaction rate, a filtration method using the component shown in FIG. 4 was employed. Specifically, the component of FIG. 4 on a weighing frame 3 was placed on the precision balance W, in place of H (heater unit) in FIG. 1. In the same manner as in Example 1, a sample from the V-1 was weighed accurately (3 g at the beginning). At this time, a 3-way select valve 4 in FIG. 4 was directed to a receptacle R by actuating the valve axis driving unit by way of the PC. In this example, the pump P-3 in FIG. 1 was used as the feed pump of a 1N aqueous sulfuric acid solution having had dissolved oxygen removed, instead of dilution water, and the opening time of the electromagnetic valve was controlled by the PC so that about 80 c.c. of the solution was charged onto a filter 1 to dissolve only the white precipitate, the resulting solution was moved to the receptacle R through the valve 4.

In the same manner as in Example 1, titration was carried out using an oxidation reduction electrode and 1/10N potassium permanganate solution. Since the receptacle R has absolutely no nozzles or channels with no use, rapid analysis and receptacle washing were performed without suffering from any of such effects as delay of liquid mixing.

The needle crystals remaining on the filter 1 were washed with the solution from a back wash feed nozzle 6 connected with the line from the pump P-3, the resulting solution was discarded through a back wash discharge nozzle 2. After a certain period of time following the discard, the valve axis was driven so that the remaining water in the filter was discarded through a waste liquor discharge nozzle 5, the valve axis was then rotated for the next analysis. The back wash liquor feed unit in FIG. 4 signifies a set of components required for backwashing the filter, and corresponds to the set of the tank of 1N dilute sulfuric acid, the pump P-3, the motor operated valve, etc., in this example. When the liquid is identical to that used for other purposes, the unit may also be used for such purposes.

The results were substantially the same as those in Example 2, and their reliability was improved remarkably over the results of analyses done by plural workers for a long period of time.

EXAMPLE 4

Operation was carried out according to the block diagram shown in FIG. 6.

In order that needle crystals on the filter were removed in the procedure of Example 3, the crystals were dissolved by dropping 10 c.c. of concentrated sulfuric acid thereto from above the filter by driving the dispenser P-2 in FIG. 1, and the resulting solution was discharged through the waste liquor discharge nozzle 5. Thereafter, the solenoid valve installed on the line of the P-3 was opened to wash the filter with 1N dilute sulfuric acid. The analytical operation was repeated for 12 hours or more by this procedure. The results were substantially the same as those in Example 2 and hence, the long-time reaction could be controlled with a high precision along the intended reaction course.

Availability in Industry

According to this invention, there is provided an apparatus for automatic analysis and a method for automatic analysis, in both of which a series of operations from the sampling into a receptacle, pretreatment, analysis and discharge of a fluid sample to the preparations of the next analysis are repeated automatically in sequence so that the time-dependent variation of the composition is traced in order, and hence, the presence of the composition variation or the course of the composition variation is confirmed or the composition variation is controlled automatically. Accordingly, this invention can favorably be applied to various industrial areas, such as reaction, distillation and discharge, where fluids involving composition variation are dealt with.

What is claimed is:

1. An automatic analytical apparatus for analyzing the composition of a fluid involving a time-dependent variation of composition, the apparatus comprising at least:
   (a) a treating receptacle;
   (b) a quantitative sampling means for taking and providing a fluid sample into said treating receptacle;
   (c) a quantitative supply means for supplying each analytical reagent necessary for the analytical operation to said treating receptacle;
   (d) a pretreatment means for subjecting the obtained sample to at least one pretreatment operation selected from the group consisting of heating, cooling, filtration, adsorption and dissolution;
   (e) a detection means for detecting the analytical course;
   (f) a signal conversion means for converting the detected signals;
   (g) a discharge means for ejecting the liquid contained in the treating receptacle;
   (h) a means for processing the analytical course detection signals, calculating analytical results, and determining the next analytical conditions, said means for determining the next analytical conditions comprises means for determining an amount of sample for the present analysis in response to the analytical result of the previous sample and means for controlling the quantitative sampling means to take and provide the amount of sample determined by the sample amount determining means into said treating receptacle; and
   (i) a control means for actuating each of the foregoing means in order according to a predetermined rule, by means of which a series of operations ranging from the sampling into the treating receptacle, pretreatment, analysis, and discharge of a fluid sample to the preparation for the next analysis are repeated automatically in sequence so that the time-dependent variation of the composition is traced in order, thus permitting the presence of the composition variation or the course of the composition variation to be confirmed or the composition variation to be controlled automatically.

2. An automatic analytical apparatus for analyzing the composition of a fluid involving a time-dependent variation of composition, the apparatus comprising at least:
   (a) a treating receptacle;
   (b) a quantitative sampling means for taking and providing a fluid sample into said treating receptacle;
   (c) a quantitative supply means for supplying each analytical reagent necessary for the analytical operation to said treating receptacle;
   (d) a pretreatment means for subjecting the obtained sample to at least one pretreatment operation selected from the group consisting of heating, cooling, filtration, adsorption and dissolution;
   (e) a detection means for detecting the analytical course;
   (f) a signal conversion means for converting the detected signals;
   (g) a discharge means for ejecting the liquid contained in the treating receptacle;
   (h) a means for processing the analytical course detection signals, calculating analytical results, and determining the next analytical conditions, said means for determining the next analytical conditions comprises means for determining an amount of sample for the present analysis in response to the analytical result of the previous sample, means for determining an initial amount of analytical reagent to be supplied to the present sample in response to the analytical result of the previous sample and the amount of the present sample, and means for controlling the quantitative sampling means and quantitative supply means to take and provide the amount of sample determined by the sample amount determining means into said treating receptacle and supply the initial amount of analytical reagent determined by the initial reagent amount determining means to said treating receptacle; and
   (i) a control means for actuating each of the foregoing means in order according to a predetermined rule, by means of which a series of operations ranging from the sampling into the treating receptacle, pretreatment, analysis, and discharge of a fluid sample to the preparation for the next analysis are repeated automatically in sequence so that the time-dependent variation of the composition is traced in order, thus permitting the presence of the composition variation or the course of the composition variation to be confirmed or the composition variation to be controlled automatically.

3. The automatic analytical method according to claim 1 or claim 2 wherein the discharge means of the liquid contained in the treating receptacle is a suction nozzle driven by an up-and-down driving mechanism provided above said receptacle.

4. The automatic analytical apparatus according to claim 1 or claim 2 wherein the detection means comprises a spectrometer for absorptiometry using ultraviolet, infrared or visible light.

5. The automatic analytical apparatus according to claim 1 or claim 2 wherein the detection means comprises a titration electrode selected from the group consisting of a potentiometric titration electrode, a polarization titration electrode, a neutralization titration electrode, and a chelatometric titration electrode.

6. A method for the automatic analysis of the composition of a fluid involving a time-dependent variation of composition, the method comprising:
(A) preparing an analytical apparatus comprising at least:
   (a) a treating receptacle;
   (b) a quantitative sampling means for taking and supplying a fluid sample into said treating receptacle;
   (c) a quantitative supply means for supplying each reagent necessary for the analytical operation to said treating receptacle;
   (d) a pretreatment means for subjecting the obtained sample to at least one pretreatment operation selected from the group consisting of heating, cooling, filtration, adsorption and dissolution;
   (e) a detection means for detecting the analytical course;
   (f) a signal conversion means for converting the detected signals;
   (g) a discharge means for ejecting the liquid contained in the treating receptacle;
   (h) a means for processing the analytical course detection signals, calculating analytical results, and determining the next analytical conditions, said means for determining the next analytical conditions comprises means for determining an amount of sample for the present analysis in response to the analytical result of the previous sample and means for controlling the quantitative sampling means to take a provide the amount of sample determined by the sample amount determining means into said treating receptacle; and
   (i) a control means for actuating each of the foregoing means in order according to a predetermined rule;
(B) taking and providing that amount of sample determined by the sample amount determining means into the treating receptacle;
(C) pretreating said fluid sample;
(D) analyzing the pretreated sample;
(E) ejecting the fluid sample having undergone the analysis from the treating receptacle; and
(F) repeating the foregoing courses (b) to (e) automatically in order, whereby the time-dependent variation of the composition is traced sequentially, permitting the presence of the composition variation or the course of the composition variation to be confirmed or the composition variation to be controlled automatically.

7. The automatic analytical method according to claim 6 wherein the means for determining the next analytical conditions comprises a means for automatically varying the amount of the sample to be taken so that the amount of the material to be analyzed in said liquid sample can be varied by referring to the analytical results of the latest sample and the amount of the present sample.

8. The automatic analytical method according to claim 6 wherein the detection means comprises a spectrometer for absorptiometry using ultraviolet, infrared or visible light.

9. The automatic analytical method according to claim 6 wherein the detection means comprises a titration electrode selected from the group consisting of a potentiometric titration electrode, a polarization titration electrode, a neutralization titration electrode, and a chelatometric titration electrode.

* * * * *

UNITED STATES PATENT AND TRADEMARK OFFICE
CERTIFICATE OF CORRECTION

PATENT NO. : 5,186,895

DATED : Feb. 16, 1993

INVENTOR(S) : Onofusa et al.

It is certified that error appears in the above-identified patent and that said Letters Patent is hereby corrected as shown below: In the title page, please add the following:

-- Related U.S. Application Data

[63] Continuation-in-part of International PCT
Application No. JP90/00790, filed on Jun. 16, 1990 --

Signed and Sealed this

Ninth Day of November, 1993

Attest:

BRUCE LEHMAN

Attesting Officer     Commissioner of Patents and Trademarks